United States Patent
Housworth et al.

(10) Patent No.: US 7,463,930 B2
(45) Date of Patent: Dec. 9, 2008

(54) IMPLANTABLE MEDICAL DEVICE PROGRAMMER MODULE FOR USE WITH EXISTING CLINICAL INSTRUMENTATION

(75) Inventors: Craig M. Housworth, Woodbury, MN (US); Nancy P. Pool, Eldorado Hills, CA (US)

(73) Assignee: Medtronic, Inc., Minneapolis, MN (US)

( * ) Notice: Subject to any disclaimer, the term of this patent is extended or adjusted under 35 U.S.C. 154(b) by 378 days.

(21) Appl. No.: 10/775,402

(22) Filed: Feb. 10, 2004

(65) Prior Publication Data
US 2004/0225337 A1 Nov. 11, 2004

Related U.S. Application Data

(63) Continuation-in-part of application No. 09/745,112, filed on Dec. 20, 2000, now abandoned.

(51) Int. Cl.
A61N 1/08 (2006.01)
(52) U.S. Cl. .......... 607/60; 600/523; 600/522; 607/32; 607/5
(58) Field of Classification Search .......... 607/60, 607/59, 32, 27, 34; 128/903, 904; 600/509, 600/522, 523
See application file for complete search history.

(56) References Cited

U.S. PATENT DOCUMENTS

| | | | |
|---|---|---|---|
| 3,991,747 A | 11/1976 | Stanly et al. | |
| 4,142,533 A | 3/1979 | Brownlee et al. | |
| 4,203,448 A | 5/1980 | Keller, Jr. | |
| 4,476,868 A | 10/1984 | Thompson | |
| 4,561,443 A * | 12/1985 | Hogrefe et al. | 607/31 |
| 4,958,632 A * | 9/1990 | Duggan | 607/11 |
| 5,052,388 A | 10/1991 | Sivula et al. | |
| 5,289,824 A | 3/1994 | Mills et al. | |
| 5,304,209 A | 4/1994 | Adams et al. | |
| 5,345,362 A | 9/1994 | Winkler | |
| 5,467,773 A | 11/1995 | Bergelson et al. | |
| 5,487,755 A | 1/1996 | Snell et al. | |
| 5,724,985 A * | 3/1998 | Snell et al. | 600/510 |
| 5,759,199 A * | 6/1998 | Snell et al. | 607/60 |
| 5,836,995 A | 11/1998 | MGraw et al. | |

(Continued)

FOREIGN PATENT DOCUMENTS

EP 0856333 8/1998

(Continued)

*Primary Examiner*—Kennedy J Schaetzle
(74) *Attorney, Agent, or Firm*—Daniel G. Chapik

(57) ABSTRACT

An external programmer module adapted for physical and electrical connection to existing clinical monitoring and/or therapy instrumentation is provided for achieving bi-directional communication with an implantable medical device (IMD). The programmer module includes telemetry circuitry necessary for communicating with an IMD and a connector that allows electrical connection to a clinical instrument such as a patient monitor or external defibrillator. The connector is adapted to connect the programmer module with the power supply of the clinical instrument and may connect the programmer module with one or more features or subsystems of the clinical instrument, such as, a central processing system, a printer, an electronic storage medium, a user interface, a communications interface, or graphical display. The programmer module is enclosed in a housing adapted for physical mating with the clinical instrument, either on the outside of the clinical instrument or within an open bay designed to receive auxiliary devices.

4 Claims, 4 Drawing Sheets

U.S. PATENT DOCUMENTS

| | | | |
|---|---|---|---|
| 5,919,141 A | 7/1999 | Money et al. | |
| 6,052,624 A | 4/2000 | Mann | |
| 6,263,245 B1 * | 7/2001 | Snell | 607/60 |
| 6,633,932 B1 * | 10/2003 | Bork et al. | 710/72 |

FOREIGN PATENT DOCUMENTS

| | | |
|---|---|---|
| WO | 9611722 | 4/1996 |
| WO | 9842407 | 10/1998 |
| WO | 0027277 | 5/2000 |

* cited by examiner

IMPLANTABLE MEDICAL DEVICE PROGRAMMER MODULE FOR USE WITH EXISTING CLINICAL INSTRUMENTATION

CROSS REFERENCE TO PRIOR APPLICATION

This application is a continuation-in-part of prior application Ser. No. 09/745,112, filed on Dec. 20, 2000, entitled "Instrumentation and Software for Remote Monitoring and Programming of Implantable Medical Devices (IMDs)", now abandoned.

FIELD OF THE INVENTION

The present invention relates generally to implantable medical devices and more particularly to an external programmer module that may be interfaced with an existing medical instrument for retrieving data or programming an implantable medical device.

BACKGROUND OF THE INVENTION

An external device, commonly known as a "programmer", is typically used for transmitting data to or from an implantable medical device (IMD). The external programmer may be used to transmit programming codes to the IMD for use by a control unit within the IMD for controlling various functions of the IMD. The external programmer may additionally be used to deliver an interrogation command to initiate receipt of data from the IMD relating to the device function or programming status or relating to physiological data collected by the implanted device. Such data transmission to and from the IMD is accomplished via a telemetric communication link established between the external programmer and the IMD.

Examples of external programmers for use with implantable cardiac pacemaker devices are generally disclosed in U.S. Pat. No. 4,550,370 issued to Baker, U.S. Pat. No. 4,236,524 issued to Powell et al., and U.S. Pat. No. 4,305,397 issued to Weisbrod, et al., all of which are incorporated herein by reference in their entirety. In addition to a control unit such as a microcomputer for executing programmable code and the necessary telemetry circuitry for communicating with the implanted device, an external programmer typically includes features such as: a user interface, e.g., a keyboard or pointing device; a graphical display such as an LCD screen which may also be used as a graphical user interface (GUI); a printer for creating printed records of transmitted data; and a portable electronic storage medium such as a floppy or compact disk drive. Advanced programmers may include a communications link for transferring data retrieved from an IMD to a central database via the Internet or a local network. An external programmer may further include an interface for receiving sensors, such as surface ECG electrodes, to allow instrumentation of the patient for real time monitoring.

While external programmers are typically provided in a carrying case for portability, a programmer may not be readily available in a particular clinical setting when needed, particularly in emergency settings. An external programmer for use with implantable cardiac stimulation devices, for example, will typically be located in a cardiology clinic and may not be readily available in an emergency room, ambulance, medical helicopter or other acute care setting. However, obtaining information about the type of implanted device that a patient may have, its current functional status, and any stored physiological data may be extremely useful to an emergency responder in understanding the patient condition and selecting the most appropriate treatment mode.

An external programmer, however, can take up valuable physical space in an already crowded medical setting. Furthermore, features included in an external programmer, such as ECG leads and interface, printing and electronic data storage capabilities, user interface, graphical display, etc., may be redundant to subsystems or functions available on other medical instruments already present in a particular clinical setting. For example, bedside patient monitoring equipment, typically will include ECG monitoring capabilities, a central processing system, a user interface, power supply, graphical display, and other electrical subsystems that may be duplicated in an external programmer. Even external emergency therapy equipment, such as external defibrillation devices, may include features and subsystems that are duplicated in an external programming device.

BRIEF SUMMARY OF THE INVENTION

The present invention merges the features of an external programmer with the features of an existing clinical monitoring or therapy instrument, such as a bedside patient monitoring console or external defibrillator or other emergency therapy delivery instrument. Redundant features and electrical subsystems normally included in an external programmer may be eliminated thereby conserving valuable space that would otherwise be taken up by a fully contained, stand-alone, external programmer. By providing at least some features of an external programmer in a modular unit that may be merged with existing medical instrumentation, valuable implanted device and patient-related information is retrievable by medical personnel without requiring a stand-alone external programmer.

The present invention provides an external programmer module adapted for physical and electrical connection to existing clinical monitoring and/or therapy instrumentation. The external programmer module includes at least the telemetry circuitry necessary for communicating with an implanted device and a connector that allows electrical connection to a clinical instrument such as a patient monitor, external defibrillator, or other clinical monitoring or therapy delivery instrumentation. The connector is adapted to connect the programmer module with an AC and/or DC power supply of the clinical instrument and preferably connects the programmer module with one or more features or subsystems of the host clinical instrument, such as, a central processing system, a printer, an electronic storage medium, a user interface, a communications interface such as a modem or network connection, and/or a graphical display. The programmer module may include control circuitry such as a microprocessor for controlling module functions and communicating with the central processing system of the host instrument. The programmer module is preferably enclosed in a housing adapted for physical mating with the clinical instrument, either on the outside of the clinical instrument or within an open bay designed to receive auxiliary devices.

In one embodiment, an external programmer module equipped with telemetry circuitry for bi-directional communication with an implanted device is adapted for connection to a clinical instrument having a power supply, a central processing subsystem, a user interface, and data storage and display features such as a graphical display, a printer, an electronic storage medium, a communications interface, and may include additional physiological monitoring modules or therapy delivery modules. Through the connection to the clinical instrument, the programmer module receives operating power from the instrument's power supply; receives commands entered on the instrument's user interface; uplinks data from an IMD upon receipt of an interrogation command entered on the instrument's user interface; and transmits uplinked data from an implanted device in response to received commands to the instrument's graphical display, printer, electronic data storage medium, central processing system, and/or the communications interface. Data retrieved from the IMD via the programmer module may thus be displayed, stored, transferred to another computer for central data storage or analysis, and/or undergo processing and analysis by the instrument's central processing system.

In another embodiment, the external programmer module includes telemetry circuitry and an ECG interface for receiving ECG electrode connections. Such a module is useful when used in conjunction with a clinical instrument lacking an ECG electrode interface.

In yet another embodiment, the programmer module includes telemetry circuitry, a central processing system, a user interface, a graphical display, and optionally an ECG electrode interface. The programmer module is adapted for physical and electrical connection to a clinical instrument including a power supply and a central processing system and may include a user interface, a display and other physiological monitoring or therapy delivery modules. The programmer module receives operating power via the connection to the clinical instrument and transfers data uplinked from an implanted device to the central processing system of the clinical instrument. The dedicated user interface and display included in the programmer module may be conveniently used to enter commands or initiate programmer module functions and observe the functional status of the module and/or retrieved data. Retrieved data may then be transferred to the clinical instrument and, under control of the central processing system, displayed, analyzed, or transferred to a printer, electronic data storage medium, or communications interface.

Thus, the present invention provides a flexible platform on which a programmer module may be designed for integration with a patient monitor or therapy delivery system wherein the programmer module may include a subset of features normally included in a stand-alone programmer and otherwise relies on features and capabilities already available in the patient monitor or therapy delivery system. The present invention thereby makes programmer functions more readily available in a variety of clinical settings without redundancy of other medical equipment functions or the extra space required for a stand-alone programmer.

DETAILED DESCRIPTION OF THE PREFERRED EMBODIMENTS

The present invention is directed toward providing external programmer functionality in a modular unit to be used in conjunction with existing clinical instruments such as patient monitors or external therapy delivery equipment. An external programmer module is intended to require less space than a stand-alone programmer and utilize functions and features already available in a clinical instrument such as display, storage, central processing, and communication links. An external programmer module used in conjunction with a clinical instrument may provide full programmer functionality, i.e. all functions or features available in a stand-alone programmer may be made available through the combination of the programmer module and the clinical instrument. Alternatively, an external programmer module used in conjunction with a clinical instrument may offer a subset of programming functions normally available in a stand-alone external programmer. For example, a programmer module may not allow full programmability of an IMD. A programmer module may be limited to interrogating an IMD without the ability to program new operating parameter values or modes. Alternatively, a programmer module may offer programmability of a limited number or range of operating parameters or modes. Furthermore, the programmer module used in conjunction with an external device may allow data retrieved from an IMD to be displayed graphically, but may or may not include additional data handling features such as data storage capabilities, data transmission to a central database, certain types of data analysis, or other data handling capabilities that may normally be available in a stand alone programmer.

The functionality of the programmer module will depend in part on the type of clinical instrument with which it is used, the intended clinical setting, and the level of training of the intended user. One of ordinary skill in the art will recognize that numerous combinations of features and functions normally included in a stand-alone programmer may be made available in a programmer module used in combination with any of a variety of clinical instruments. The present invention provides a platform on which a programmer module is implemented, wherein the programmer module includes at least telemetry circuitry for bi-directional communication with an IMD, and may include any number of additional subsystems such as data storage and handling subsystems or patient monitoring interfaces, that are desired but may be unavailable on the clinical instrument with which the programmer module will be used. The programmer module platform allows for physical and electrical connection of the programmer module with a clinical instrument such that programmer functionality is readily available in a particular clinical setting but is advantageously merged with other clinical instrumentation to thereby eliminate the bulkiness and functional redundancies of a stand-alone programmer.

Figure 1:
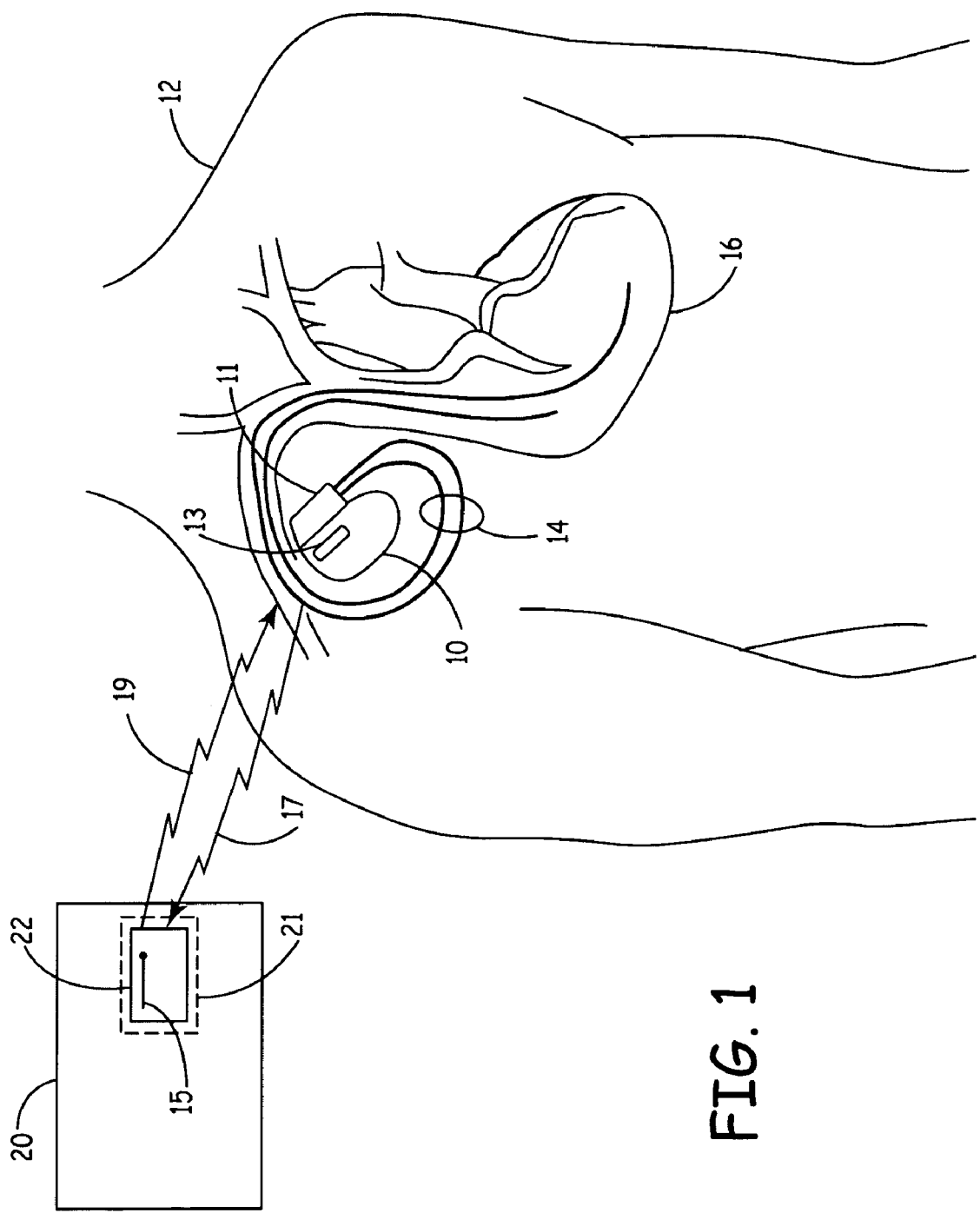
FIG. 1 is an illustration of an implantable medical device in telemetric communication with an external programmer module merged with a clinical instrument in accordance with the present invention.

FIG. 1 is an illustration of an implantable medical device in telemetric communication with an external programmer module merged with a clinical instrument in accordance with the present invention. An implantable medical device (IMD) 10 is shown implanted in the body of a patient 12. The present invention may be implemented for use with a variety of programmable IMDs, including cardiac stimulation devices, cardiac monitoring devices, neuromuscular stimulators, implantable drug pumps, or the like. For the sake of illustration, IMD 10 is shown here as a cardiac stimulation device coupled to a set of leads 14 used for positioning electrodes and optionally other physiological sensors in operative relation to the patient's heart 16. Leads 14 are coupled to IMD 10 via a connector block 11.

IMD 10 contains an operating system that may employ a microcomputer or a digital state machine for timing cardiac sensing and stimulation functions in accordance with a programmed operating mode. The IMD 10 also contains sense amplifiers for detecting cardiac signals, patient activity sensors or other physiologic sensors for sensing the need for cardiac output, and pulse generating output circuits for delivering cardiac stimulation pulses to at least one chamber of the heart 16 under control of the operating system in a manner well known in the prior art. The operating system includes memory registers or RAM for storing a variety of programmed-in operating mode and parameter values that are used by the operating system. The memory registers or RAM may also be used for storing data compiled from sensed cardiac activity and/or relating to device operating history or sensed physiologic parameters for telemetry out on receipt of a retrieval or interrogation instruction. All of these functions and operations are well known in the art, and many are employed in other programmable IMDs to store operating commands and data for controlling device operation and for later retrieval to diagnose device function or patient condition.

In accordance with the present invention, IMD 10 is in telemetric communication with external programmer module 22. Programmer module 22 is adapted for physical and electrical connection with a clinical instrument 20 which may be embodied as a bedside patient monitoring console, a therapy delivery device such as an external defibrillator, or other medical instrument that includes monitoring and/or therapy delivery capabilities. Instrument 20 includes an interface or bay 21 for receiving module 22 and providing electrical and physical connection between instrument 20 and module 22.

Programming commands or data are transmitted between an IMD RF telemetry antenna 13 and an external RF telemetry antenna 15 associated with the external programmer module 22. The external RF telemetry antenna 15 may be contained in a programmer RF head so that it can be located close to the patient's skin overlying the IMD 10. Such programmer RF heads are well known in the art. See for example the previously incorporated '370 patent to Baker. The programmer module 22 may be designed to universally program IMDs that employ conventional ferrite core, wire coil, RF telemetry antennas known in the prior art and therefore also have a conventional programmer RF head and associated software for selective use with such IMDs.

Alternatively, the external RF telemetry antenna 15 can be located on the case of the external programmer module 22, and the programmer module 22 can be located some distance away from the patient 12. For example, external programmer module 22 and external RF telemetry antenna 15 may be integrated with instrument 20 located a few meters or so away from the patient 12 and utilize long-range telemetry systems. Such long-range telemetry systems would allow bidirectional communication between IMD 10 and external programming module 22 when IMD 10 is within a communication range of programming module 22. Moreover, the patient 12 may be active and could be exercising on a treadmill or the like during an uplink telemetry interrogation of real time ECG or physiologic parameters. Telemetry systems that do not require the use of a programmer RF head are generally disclosed in U.S. Pat. No. 6,240,317 Villaseca et al., U.S. Pat. No. 6,169,925 issued to Villaseca et al., and U.S. Pat. No. 6,482,154, issued to Haubrich et al., all of which patents are incorporated herein by reference in their entirety.

In an uplink telemetry transmission 17, the external RF telemetry antenna 15 operates as a telemetry receiver antenna, and the IMD RF telemetry antenna 13 operates as a telemetry transmitter antenna. Conversely, in a downlink telemetry transmission 19, the external RF telemetry antenna 15 operates as a telemetry transmitter antenna, and the IMD RF telemetry antenna 13 operates as a telemetry receiver antenna. Both RF telemetry antennas are coupled to a transceiver comprising a transmitter and a receiver.

Figure 2:
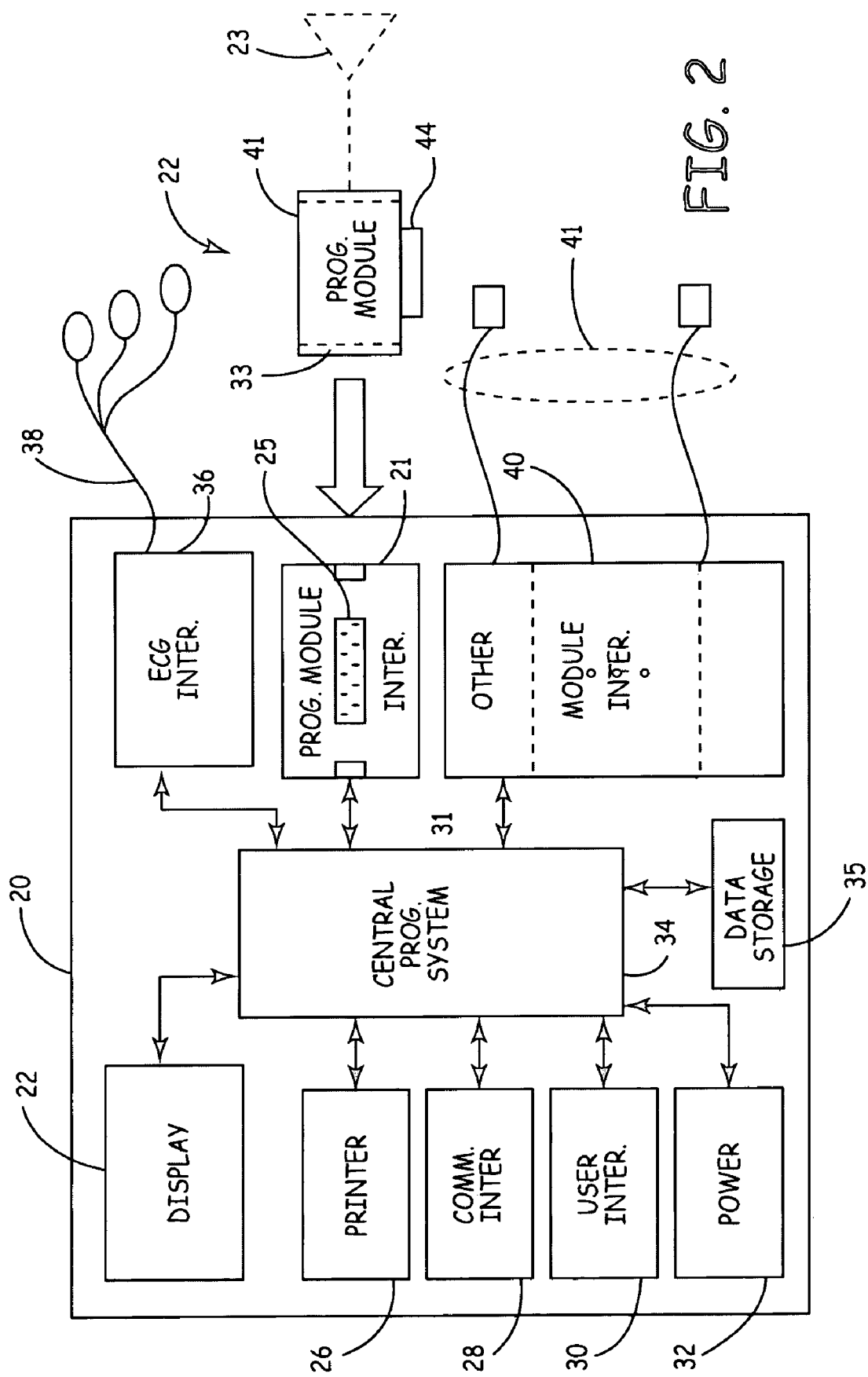
FIG. 2 is a block diagram of one embodiment of the clinical instrument shown in FIG. 1 with which an external programmer module may be integrated.

FIG. 2 is a block diagram of one embodiment of the clinical instrument shown in FIG. 1 with which an external programmer module may be integrated. Clinical instrument 20 typically includes a central processing system 34 which may be in the form of a microcomputer having a microprocessor and associated memory for storing programmable code executed for controlling various functions of instrument 20. Instrument 20 further includes a display 24 which may be in the form of a graphical user interface on an LCD screen; a strip-chart recorder or printer 26, a hardwired or wireless communications interface 28 which may be provided as a modem or local network connection; a user interface 30 which may be provided as a keyboard, mouse, or other pointing device; an electronic data storage unit 35 such as a compact disk drive for storing data electronically; and a power supply 32 which may be provided as a battery and/or AC connection to external line voltage. Central processing system 34 is coupled to each of these components via appropriate signal lines for controlling instrument 20 functions and providing power from power supply 32 to the various components and subsystems included in instrument 20 as required.

For the purposes of the present invention, the detailed architecture of instrument 20 and various components included in instrument 20 may correspond to any commercially available monitoring or therapy delivery systems. Modular systems are available having a number of "add-on" features that allow the addition of sensors, such as pulse oximetry sensors, ECG electrodes, respiration sensors, blood pressure sensors, $CO_2$ sensors, or other physiological sensors. Such sensors are coupled to instrument 20 via an appropriate interface connection that provides analog or digital connection to central processing system 34 to allow display, storage or analysis of data received from sensors. Such interfaces are represented collectively by a bank of other module interfaces 40 coupled to corresponding sensors 41 shown in FIG. 2.

In the embodiment shown the instrument 20 is a manual or automated external defibrillator (AED), a dedicated ECG interface module 36 is shown for receiving ECG electrodes 38 such that a patient's ECG signal is available for analysis, display and/or storage. Examples of commercially available systems equipped with interfaces to support different types of physiological sensors include GE Medical monitoring systems such as the Solar® 8000 or Medtronic Physio-Control external defibrillator/monitors such as the Lifepak® 12. Adding IMD programming capabilities to a defibrillator allows caregivers to obtain information from and about an IMD without requiring personnel to carry an excessive amount of additional equipment.

In accordance with the present invention, instrument 20 includes a programmer module interface 21 for receiving programmer module 22. Programmer module interface 21 is depicted as an open bay including a receptacle 25 for receiving a connector 44 provided on programmer module 22 to achieve electrical connection between instrument 20 and module 22. Interface 21 may include mechanically engaging or interlocking members 31 for physically engaging corresponding members 33 located on housing 41, which encases module 22. Such mechanical engaging members may include spring-loaded clamps or levers or interlocking members that may be engaged upon sliding module 22 into interface 21. Engaging members 31 of host instrument 20 are shown in FIG. 2 simply as flanges for interlocking with corresponding grooves formed in housing 41 as engaging members 33. A variety of locking mechanisms could be used for mechanically coupling the housing 41 of programmer module 22 within interface 21. The design of engaging members 33 on housing 41 of module 22, and to some degree the size and shape of housing 41, will be dictated by the specification of the host instrument 20. Examples of mounting mechanisms for portable electronic devices that may be adapted for use with the present invention are generally disclosed in U.S. Pat. No. 6,594,146 issued to Frangesch et al., incorporated herein by reference in its entirety.

In alternative embodiments, mechanical engaging members and receptacle 25 may be located on the outer surface of instrument 20 rather than within an interface configured as an open bay as depicted in FIG. 2. As such, module 22 may be mounted on a side, top, or bottom of instrument 20 such that connector 44 is mated with receptacle 25.

Receptacle 25 is configured to allow electrical connection of programmer module 22, via connector 44, to the central processing system 34 and thereby to the various subsystems or components of instrument 20 that may perform useful functions in conjunction with the transmission or retrieval of data to or from an IMD 10 via programmer module 22. Such functions may include displaying retrieved data on display 24, printing retrieved data on printer 26, transferring data to another computer or network via communication interface 28, or storing data in an electronic data storage medium via data storage unit 35.

Data received from programmer module 22 may additionally be analyzed by central processing system 34 upon execution of program code installed in central processing system 34 for use with programmer module 22. Thus the present invention allows installation of software into the central processing system 34 of instrument 20 that may be used for controlling functions performed by programmer module 22 and the transfer of data between programmer module 22 and the various instrument components such as display 24, printer 26, communications interface 28, user interface 30, and data storage unit 35. Furthermore, software may be installed into central processing system 34 for processing and analyzing data received from programmer module 22.

Programmer module 22 includes a connector 44 adapted for connection to programmer module interface receptacle 25 to allow electrical connection between programmer module 22 and instrument 20. Connections made between connector 44 and receptacle 25 include at least a power supply connection such that power supply 32 may be utilized by programmer module 22 to power circuitry within programmer module 22. The need for a redundant power supply within programmer module 22 is thereby eliminated.

Additional connections made between connector 44 and receptacle 25 preferably include a data bus connection to allow the transfer of data between programmer module 22 and central processing system 34. Commands entered by medical personnel using user interface 30 may be transferred to programmer module 22 under the control of central processing system 34. For example, an interrogation command may be entered to allow device and patient-related information to be uplinked from an IMD to programmer module 22 and thereafter transferred via a data bus connection to central processing system 34 for display, storage, printing or analysis using one more of the other subsystems included in instrument 20.

In FIG. 2, programmer module 22 is optionally coupled to a programming radio-frequency (RF) head 23. As noted previously, depending on the type of telemetry circuitry included in programmer module 22, a programmer RF head 23 may or may not be necessary. Telemetry systems utilizing a programmer RF head and long-range telemetry systems which eliminate the need for a programmer head and allow bi-directional telemetry transmission when the IMD is within a communication range of the external programming or monitoring device are described in the previously-incorporated patents cited herein. Preferably, modern telemetry systems that eliminate the need for a programmer RF head are used to thereby reduce the number of components needed for use with the programmer module 22. Furthermore, such long-range telemetry systems may automatically establish a telemetry link with an implanted device that comes within a communication range of the external programming device. An external programmer module 22 incorporated in a clinical instrument 20 may advantageously retrieve IMD identification information automatically for display on instrument 20 without requiring input from a user and thereby alert medical personnel to the presence and type of IMD implanted in a patient.

Figure 3:
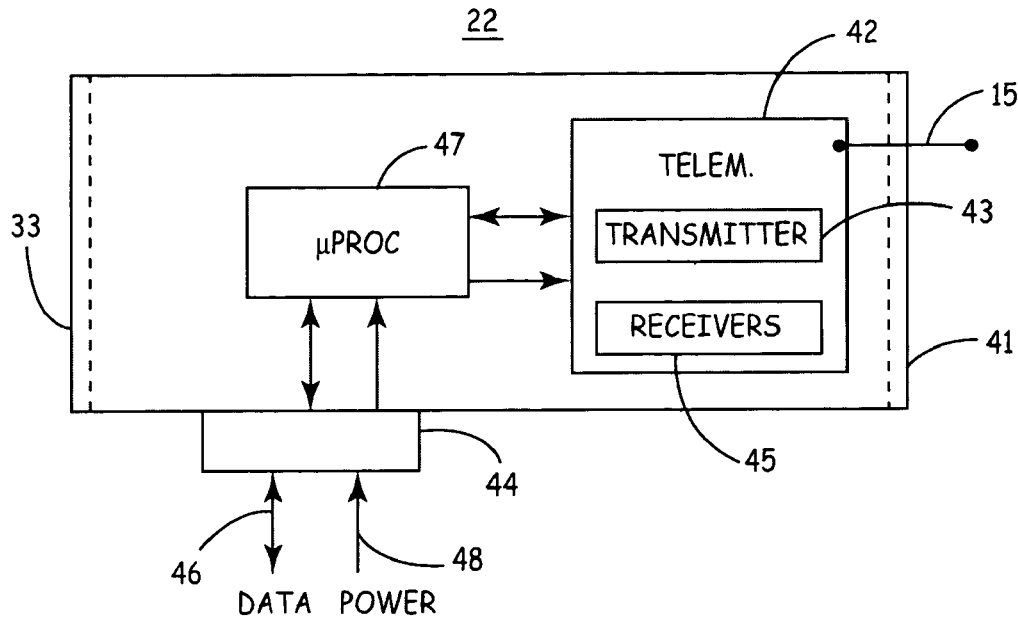
FIG. 3 is a block diagram of a programmer module adapted for use with a clinical instrument as shown in FIG. 2.

FIG. 3 is a block diagram of a programmer module 22 adapted for use with a clinical instrument as shown in FIG. 2. Programmer module 22 is enclosed in a housing 41. As noted previously, housing 41 may be provided with mechanical engaging members 33 for physical connection to instrument 20. Within housing 41, programmer module 22 includes at least a telemetry circuit 42 electrically coupled to connector 44. Telemetry circuit 42 may correspond to known telemetry systems used for bi-directional communication with IMDs. Generally, telemetry circuit 42 includes an external RF telemetry antenna 15 coupled to an antenna driver circuit, a transmitter 43 for use in downlink transmissions and a receiver 45 for use in uplink transmissions.

As described above, connector 44 is adapted to provide connectivity to power source 32 included in instrument 20 via a power line 48 and to central processing system 34 via a data bus 46 for controlling telemetry circuit 42 functions and transferring data to telemetry circuit 42, such as an interrogation command, to be downlinked to IMD 10 or for receiving data uplinked from IMD 10. Power line 48 and data line 46 are coupled to connector 44 via receptacle 25 of instrument 20. Operation of transmitter 43 and receiver 45 under the control of a microcomputer and software is known in the art and described in the above-incorporated patents.

Programmer module 22 may include control circuitry 42, shown in FIG. 3 as a microprocessor 47, for controlling telemetry circuit 42 functions and coordinating communication with the central processing system 34 of host instrument 20. While central processing system 34 may be enabled to control module 22 functions, it is preferable to include central control circuitry 42 in module 22 to limit the burden placed on the host instrument central processing system 34.

It is recognized that a single programmer module may be used for telemetric communication with more than one type or model of IMD. Accordingly, it may be desirable to include an expansion cartridge containing EPROMs or the like for storing software programs to control module 22 to operate in a particular manner corresponding to a given type or generation of IMD, as is known for use with stand-alone external programmers. Alternatively, software programs for controlling module 22 may be loaded into the central processing system 34 of the clinical instrument 20 via a CD-ROM, floppy disk drive, or a communications link for controlling module 22 in accordance with the type of IMD to be interrogated or programmed.

Figure 4:
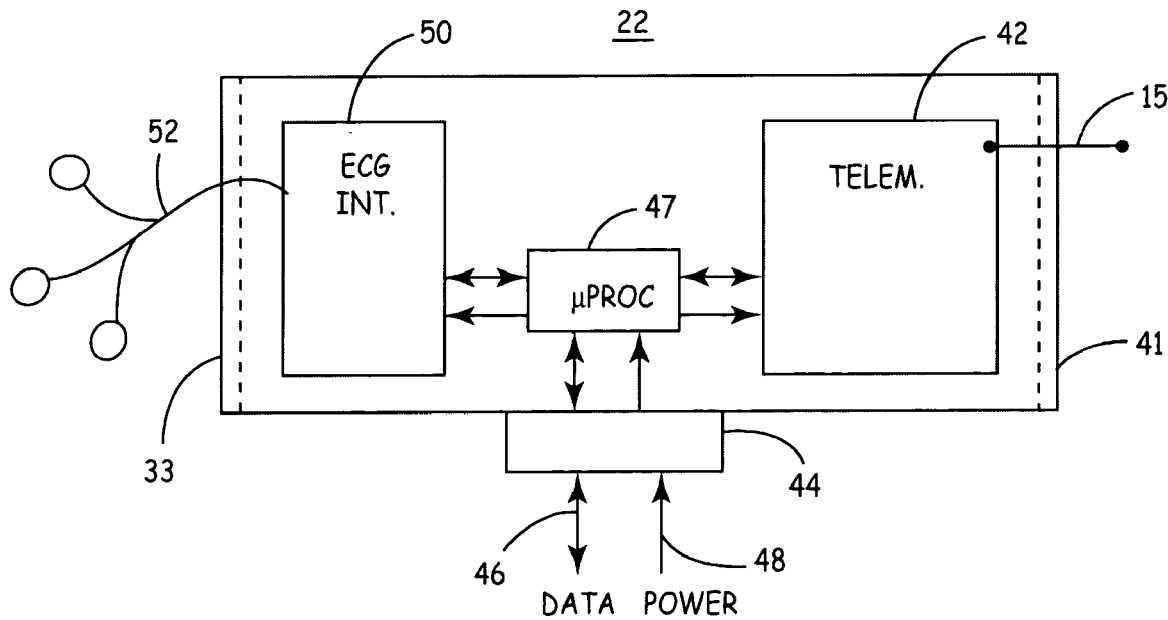
FIG. 4 is a block diagram of an alternative embodiment of a programmer module including an ECG interface.

In other embodiments, programmer module 22 may include subsystems or features in addition to telemetry circuitry 42 that may not be available in the particular medical instrument with which module 22 will be used. For example, as shown in FIG. 4, programmer module 22 may include an ECG interface 50 for coupling to ECG electrodes 52 to allow monitoring of a patient's ECG if ECG monitoring capabilities are not available from instrument 20. ECG signals received on electrodes 52 by interface 50 may be transferred to instrument 20 directly via data bus 46 for display, printing, storage, transfer to a central database, or analysis by central processing system 34. Alternatively, ECG signals may be transferred to instrument 20 under the control of microprocessor 47. Power required for circuitry included in interface 50 may be provided from instrument 20 via power line 48.

Figure 5:
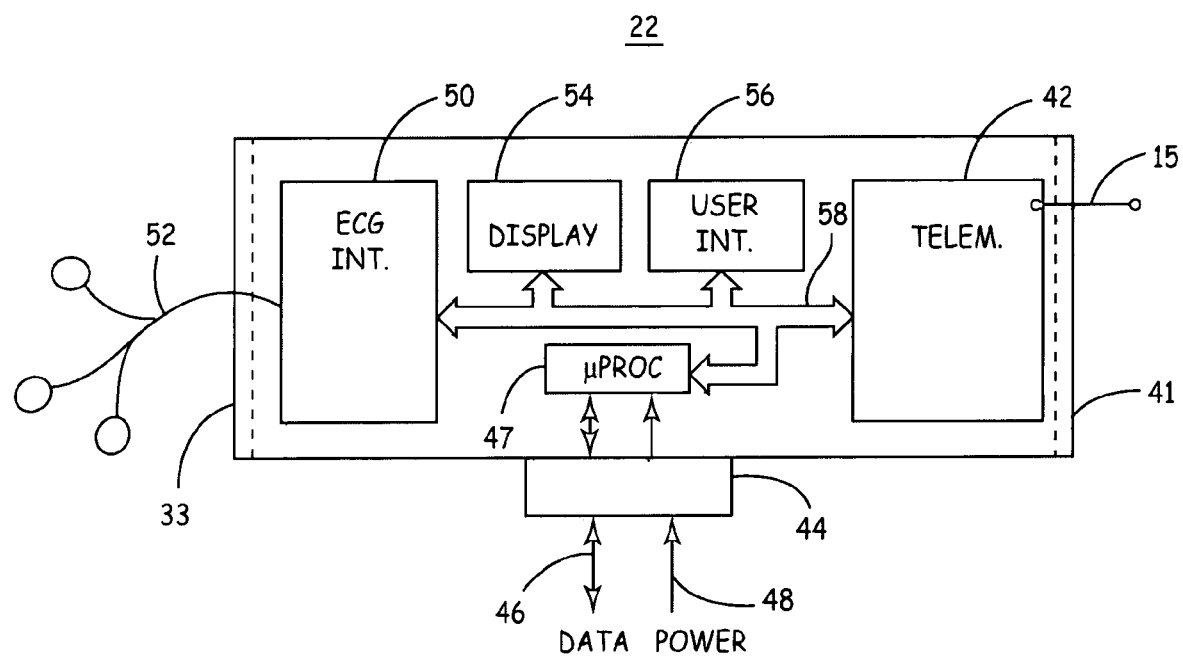
FIG. 5 is a block diagram of yet another embodiment of a programmer module including a display and a user interface.

In yet another embodiment, as shown in FIG. 5, programmer module 22 may include a display 54 and a user interface 56. Display 54 may include indicator lights or sounds to inform a user when module 22 is performing or completing a telemetry operation. Display 54 may additionally or alternatively include an LCD screen or graphical user interface to allow data retrieved from IMD 20 to be displayed in a numerical, tabular, graphical or waveform format. The display of data or information on display 54 may be controlled by central processing system 34 of instrument 20. Preferably, control circuitry 47 is included in module 22 for coordinating and controlling function between display 54, user interface 56, ECG interface 50, and telemetry circuit 42 and communicating with host instrument central processing system 34.

The user interface 56 allows a user to enter commands or initiate functions directly on module 22 via a data bus 58 linking telemetry circuit 42 with the user interface 56 and display 54 under the control of microprocessor 47. In some embodiments, programmer module 22 may be equipped with a user interface that allows simplified user control of certain functions of programmer module 22. For example, a user interface may include one or more dedicated buttons or touch pads for selecting specific commands or functions at the touch of a button without having to enter commands via the instrument's user interface 30. Such commands may include an interrogation command, a print command, a suspend all therapies command, a restore programmed operating mode command, or the like. In other embodiments, user interface 56 may allow greater interaction between a user and programmer module 22 for entering programmable parameters or initiating programmer module 22 functions. For example, user interface 56 may be a pointing device for use with a graphical user interface to initiate any of a number of functions available from the combination of programmer module 22 and instrument 20 or entering programmable operating parameters or modes for programming into IMD 10.

The programmer modules depicted in FIGS. 3 through 5 are intended to illustrate various combinations of features that may be incorporated within a programmer module. As noted previously, the number of features or subsystems included in programmer module 22 may be any of a subset of the features included in stand-alone programmers known in the art and may depend on the features available from the instrument with which module 22 is intended to be used. Other subsystems that may be included in programmer module 22 include, but are not limited to, a printer, a communications link to a central database, an electronic data storage medium, a battery, therapy delivery circuitry such as pulse generating circuitry for pacing or defibrillating the heart, or other physiological sensor interfaces.

A programmer module 22 adapted for use with a clinical monitor or therapy delivery instrument may be capable of a limited number of programming functions compared to a stand-alone programmer. Because a programmer module 22 may be used in a clinical setting wherein medical personnel may not be fully trained or qualified to program IMD functions or parameters, programmer module 22 may be limited to performing interrogation and real-time data retrieval from an IMD. In other cases, a limited set of programmable functions, such as certain operating modes or suspension or disabling of therapy delivery by the IMD, may be available to a user by entering commands or making selections using the user interface 30 of instrument 20 or a dedicated user interface 56 included in programmer module 22.

Thus a programmer module adapted for use with a clinical instrument to allow programmer functionality to be readily available in a variety of clinical settings has been described. Using the platform described, a programmer module may be physically and electrically coupled to clinical instrument such that any or all stand-alone programmer functions and features are available through the combination of the programmer module and the clinical instrument. Others having skill in the art and the benefit of the teachings provided herein may conceive of numerous variations to the embodiments described herein without departing from the scope of the invention. The detailed descriptions provided herein, therefore, are to be considered exemplary rather than limiting with regard to the following claims.

The invention claimed is:

1. A module adapted for use with a clinical instrument, the clinical instrument having a user interface, to provide at least a subset of programmer functionality for an implantable medical device, the module comprising:

a telemetry circuit for telemetric communication with an implantable medical device to interrogate the implantable medical device in retrieval of data;

a connector connected to the telemetry circuit and electrically coupled to an electrical power source included in the clinical instrument, wherein the telemetry circuit is powered by the clinical instrument; and means for coordinating real-time communication between the telemetry circuit and the clinical instrument user interface to cooperatively uplink data from the implantable medical device upon receipt of an interrogation command entered on the clinical instrument user interface.

2. The module of claim 1 wherein the communication coordinating means allows downlink data and control commands to be transferred from a central processing system included in the clinical instrument to the telemetry circuit and uplinked telemetry data from an implanted medical device to be transferred from the telemetry circuit to the central processing system included in the clinical instrument.

3. The module of claim 1, wherein the clinical instrument is selected from a group consisting of a bedside patient monitoring console and an external defibrillator.

4. The module of claim 1, wherein the clinical instrument user interface has a display selected from the group consisting of an LCD screen, a strip chart recorder, and a printer.

* * * * *